(12) United States Patent
Grell et al.

(10) Patent No.: US 12,326,432 B2
(45) Date of Patent: Jun. 10, 2025

(54) ELECTRICAL SENSING OF GASES IN PACKAGED PRODUCTS AND MONITORING FRESHNESS OR CONDITION OF PERISHABLE PRODUCTS

(71) Applicant: BLAKBEAR LTD, London (GB)

(72) Inventors: Maximilian Michael Grell, London (GB); Michail Kasimatis, London (GB); Giandrin Barandun, London (GB)

(73) Assignee: BLAKBEAR LTD, London (GB)

( * ) Notice: Subject to any disclaimer, the term of this patent is extended or adjusted under 35 U.S.C. 154(b) by 292 days.

(21) Appl. No.: 17/923,328

(22) PCT Filed: May 6, 2021

(86) PCT No.: PCT/GB2021/051100
§ 371 (c)(1),
(2) Date: Nov. 4, 2022

(87) PCT Pub. No.: WO2021/224630
PCT Pub. Date: Nov. 11, 2021

(65) Prior Publication Data
US 2023/0221295 A1    Jul. 13, 2023

(30) Foreign Application Priority Data
May 6, 2020   (GB) ...................................... 2006737

(51) Int. Cl.
*G01N 33/02*   (2006.01)
*G01N 27/22*   (2006.01)

(52) U.S. Cl.
CPC ........... *G01N 33/02* (2013.01); *G01N 27/223* (2013.01); *G01N 27/226* (2013.01)

(58) Field of Classification Search
CPC ...... G01N 33/02; G01N 27/22; G01N 27/223; G01N 27/226; G01N 27/225; G01N 27/12;
(Continued)

(56) References Cited

U.S. PATENT DOCUMENTS

| | | |
|---|---|---|
| 5,621,162 A | 4/1997 | Yun et al. |
| 2016/0178553 A1 | 6/2016 | Bommarito et al. |

(Continued)

FOREIGN PATENT DOCUMENTS

| | | | | |
|---|---|---|---|---|
| CN | 106091559 A | * | 11/2016 | ............. A23L 3/001 |
| EP | 2708878 A1 | | 3/2014 | |

(Continued)

OTHER PUBLICATIONS

International Search Report and The Written Opinion of The International Searching Authority from corresponding international PCT application, PCT/GB2021/051100, dated Sep. 13, 2021, 18 pages.
(Continued)

*Primary Examiner* — Son T Le
(74) *Attorney, Agent, or Firm* — Tucker Ellis LLP; Michael G. Craig

(57) ABSTRACT

There is provided a perishable goods monitoring system for monitoring the freshness or condition of a perishable product encapsulated within a package, the system comprising a sensor device, a wireless communication reader device and a processing module, said sensor device comprising a fibrous hydrophilic material based electrical sensor and a wireless communication tag chip coupled thereto and being configured to be incorporated in or on a said package, said wireless communication reader device being configured for wireless communication with said wireless communication tag by means of wireless communication technology when said reader device is within a predetermined distance of said
(Continued)

tag, and said processing module being configured to receive sensor data from said sensor, via said reader device, correlate said sensor data against a stored calibration data set associated with said perishable product and determine thereby data representative of freshness of said perishable product.

20 Claims, 5 Drawing Sheets

(58) Field of Classification Search
CPC ........ G01N 27/121; H04W 4/35; H04W 4/80; G06K 19/0717; G06K 19/07758; G06K 7/10386; G06Q 10/087
See application file for complete search history.

(56) References Cited

U.S. PATENT DOCUMENTS

| | | | |
|---|---|---|---|
| 2017/0038325 A1 | 2/2017 | Takashmia et al. | |
| 2017/0160005 A1* | 6/2017 | Park | G01N 33/02 |
| 2017/0356899 A1 | 12/2017 | Guder et al. | |
| 2018/0285894 A1 | 10/2018 | Kankainen et al. | |
| 2018/0342006 A1 | 11/2018 | Biernath et al. | |
| 2019/0387375 A1 | 12/2019 | Gao | |
| 2021/0123878 A1* | 4/2021 | Lim | G01N 27/221 |
| 2022/0323997 A1* | 10/2022 | Pawluczyk | B07C 5/3422 |

FOREIGN PATENT DOCUMENTS

| | | |
|---|---|---|
| EP | 3168608 A1 | 5/2017 |
| SU | 1758533 A1 | 8/1992 |
| WO | 2005071402 A1 | 8/2005 |
| WO | 2010054420 A1 | 5/2010 |

OTHER PUBLICATIONS

United Kingdom Search Report from related Great Britain Application No. GB2006737.7, dated Oct. 7, 2020, 5 pages.
Barandun et al., "Cellulose Fibers Enable Near-Zero-Cost Electrical Sensing of Water-Soluble Gases," ACS Sensors, May 8, 2019, 8 pages, https://pubs.acs.org/doi/10.1021/acssensors.9b00555.
Han et al., "Carbon Nanotube Based Humidity Sensor on Cellulose Paper, The Journal of Physical Chemistry C," Oct. 18, 2012, pp. 22094-22097, vol. 116, No. 41, DOI: 10.1021/jp3080223.

* cited by examiner

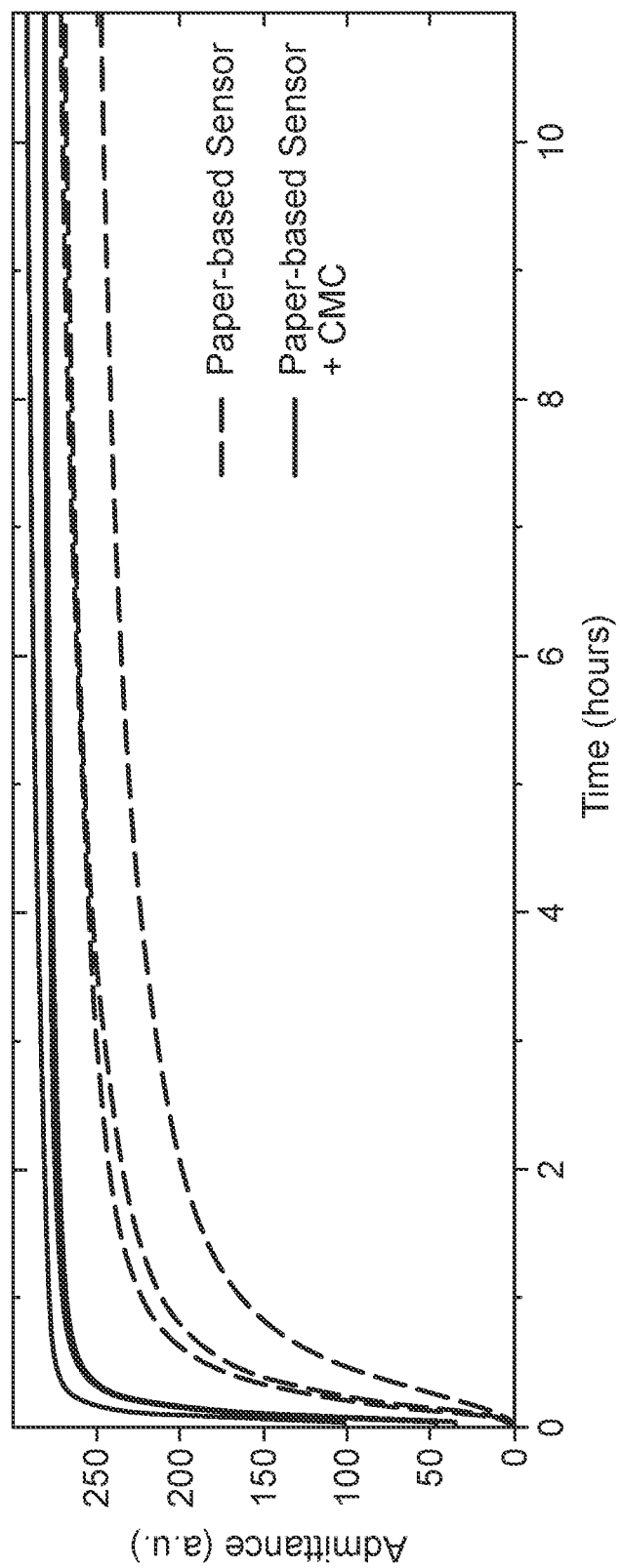

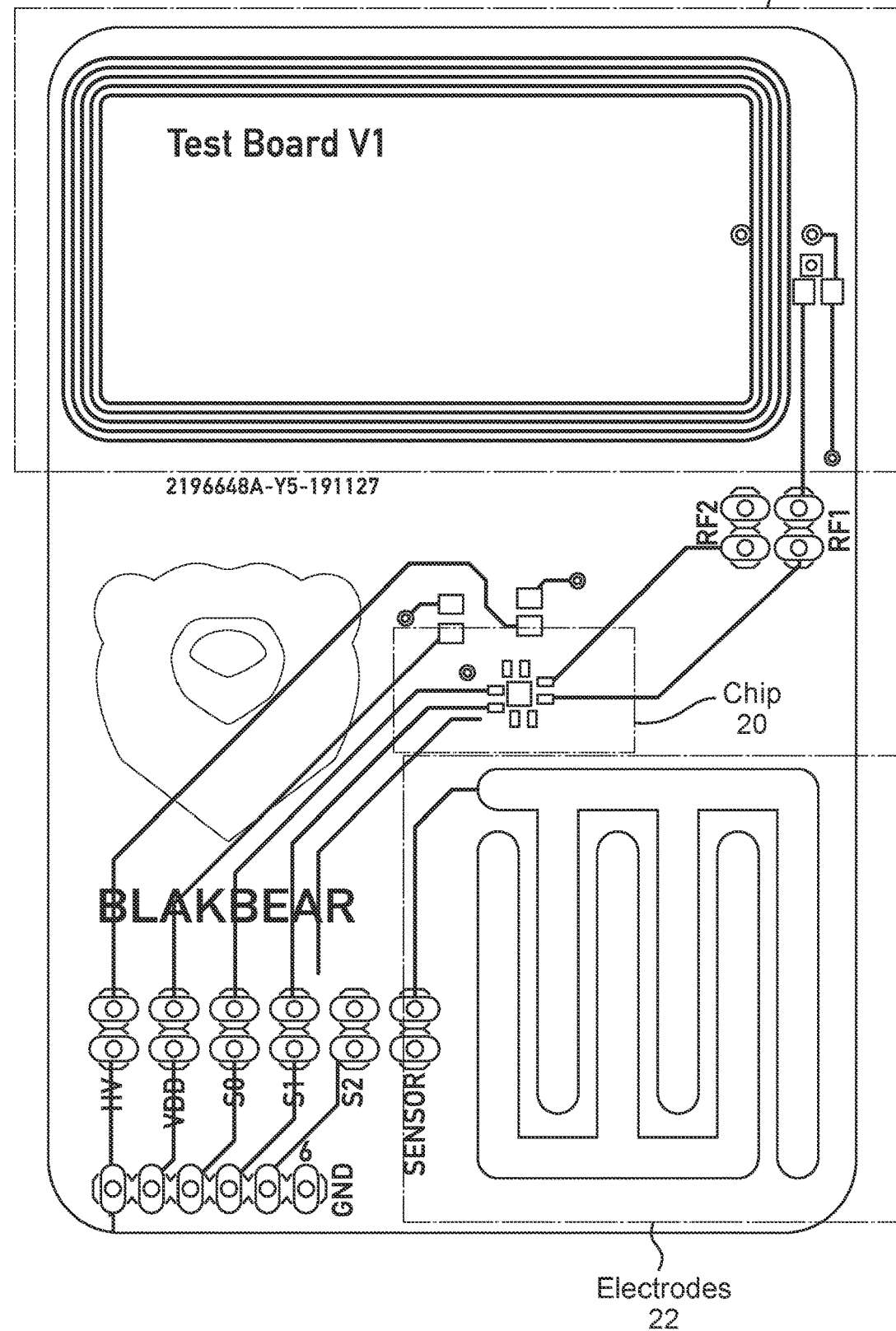

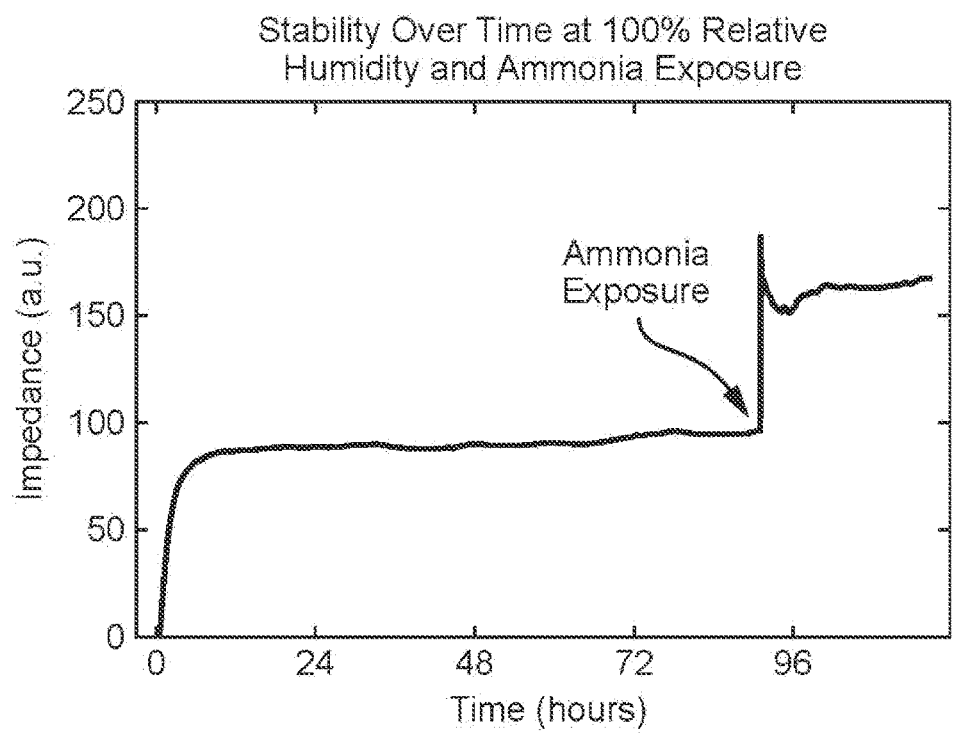
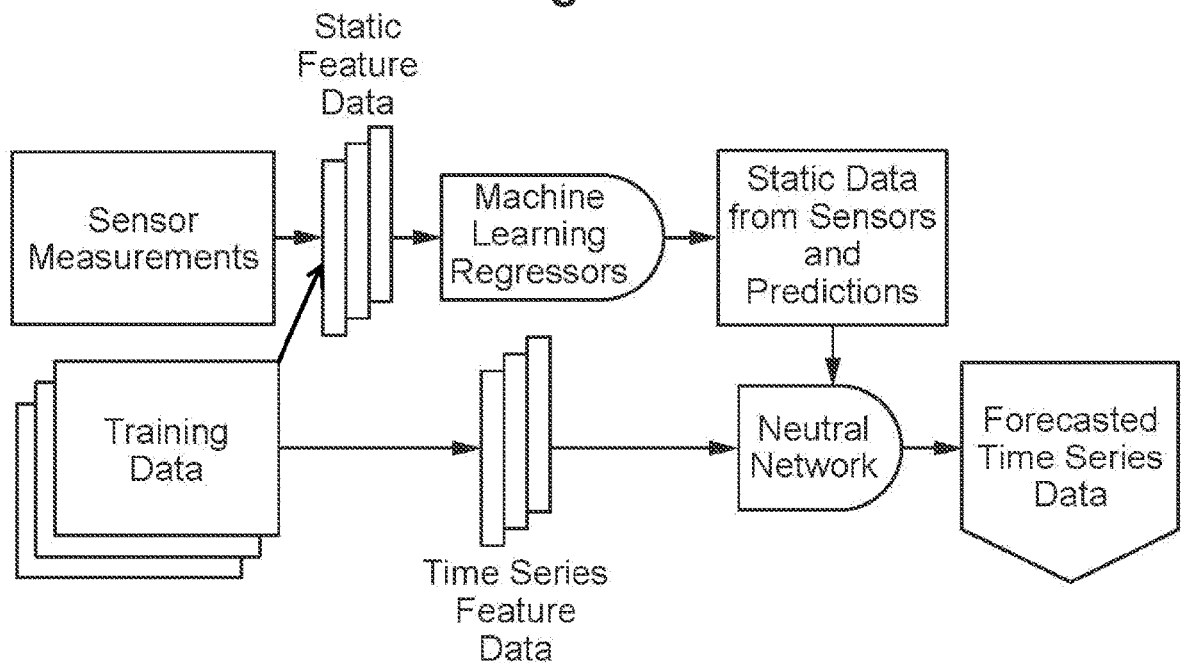

ELECTRICAL SENSING OF GASES IN PACKAGED PRODUCTS AND MONITORING FRESHNESS OR CONDITION OF PERISHABLE PRODUCTS

CROSS-REFERENCE TO RELATED APPLICATIONS

This application is a national phase application of International Application No. PCT/GB2021/051100, filed May 6, 2021, which claims priority to Great Britain Patent Application Serial No. 2006737.7, filed May 6, 2020, all of which are incorporated herein by reference.

BACKGROUND

This invention relates generally to electrical sensing of gases in packaged products and monitoring freshness or condition of perishable products such as pharma products, foodstuffs or cosmetics; and, more particularly but not necessarily exclusively, to a system and method for electrical sensing of water-soluble gases, such as ammonia, trimethylamine or carbon dioxide, within an enclosed package for use in monitoring freshness or condition of perishable products, and/or detecting changes in the composition of the atmosphere inside enclosed packages, including (but not limited to) detection of leakages and/or toxic compounds.

Food waste is a major global problem with significant economic and environmental consequences. Around 30% of all food produced for human consumption is thrown away each year, and food waste by consumers is a major contributor.

The freshness of packaged foods is estimated by the use-by date that appears on the packaging. The use-by date is an approximation for the date on which a perishable product may no longer be edible. However, this does not accurately reflect the state of freshness of the consumable, which is dependent, not only on the formulation and packaging, but also on processing and storage conditions. Nevertheless, many consumers throw away food solely because it is close to, or past, its use-by date, regardless of its actual freshness and/or edibility.

A more accurate alternative to the use-by date involves the integration of disposable sensors in the packaging, a method known as intelligent or 'smart' packaging. Sensors help to monitor the state of the perishable goods and communicate their condition to the user in real time. Such technologies range from relatively simple and qualitative temperature-time indicators to sophisticated and quantitative chemical monitors that measure the decomposition gases in packaged foods.

Despite the overwhelming advantages associated with the use of smart packaging, there are numerous reasons as to why freshness sensors are not widely integrated into mainstream food packaging. Firstly, existing smart packaging solutions are not commercially viable because they increase the cost of the packaging (in comparison with conventional packaging) by over 100%. Furthermore, in some, more complex, solutions, integration of sensors into packaging requires a complex (and costly) fabrication process, whereas the lower-cost solutions or colorimetric indicators are difficult to use accurately and are, at best, semi-quantitative. Still further, existing solutions are not fully compatible with digital platforms, i.e. the output generated is not electrical and/or cannot be easily digitized.

It is clearly desirable, therefore, to provide a commercially viable spoilage sensor (or freshness monitor) that is substantially non-destructible, (optionally) flexible (as most packaging has curved surfaces), compatible with existing packaging fabrication technologies and, most importantly, ultra-low (ideally near zero) cost. Furthermore, it would be desirable for such a sensor to be biodegradable and/or contain nontoxic materials (i.e. no metals, semiconductors, etc.) to prevent contamination of food and reduce/eliminate environmental impact.

Aspects of the present invention seek to address at least one or more of the above-mentioned issues.

SUMMARY

In accordance with a first aspect of the invention, there is provided a sensor device for sensing water-soluble gases in a perishable goods (e.g. food, pharma, cosmetics or any other product that changes or emits gases over time) monitoring system, the sensor device comprising a substrate incorporating a sensor interface including an ADC (analog-to-digital converter), the sensor interface being electrically coupled to a set of electrodes, the sensor device further comprising a strip of fibrous hydrophilic material coupled, on a surface thereof, to said set of electrodes.

The fibrous hydrophilic material preferably comprises cellulose paper or fabric. In an exemplary embodiment, wherein said monitoring system comprises a wireless communication (e.g. RFID or BLE) reader device (e.g. smartphone), the sensor interface may comprise a wireless communication tag and the substrate (e.g. PCB) may further incorporate an antenna coupled to the tag.

Beneficially, the strip of fibrous hydrophilic material may be covered or coated with a thin film or foil of hydrophobic, gas permeable material, such as PTFE. In a preferred exemplary embodiment, the strip of fibrous hydrophilic material may have a thin film or foil of hydrophobic, gas permeable material adhered thereto by, for example, a spray mount adhesive. Additionally or alternatively, individual fibres of the fibrous hydrophilic material may be coated (e.g. sprayed) with a thin layer of an additive (e.g. glutaraldehyde, EDC-NHS or sodium peroxide) to enhance sensitivity or selectivity of the sensor. Optionally, the fibrous hydrophilic material may be adhered, on a surface thereof, to said set of electrodes by means of a spray mount adhesive.

Additives (e.g. cellulose derivatives) that can tune hydrophilic materials to exhibit responses to humidity and e.g. increase signal stability and decrease response time. For example, carboxymethyl cellulose (CMC) can be used, in varying quantities, as an additive to change the response of the hydrophilic material to humidity so as to improve signal stability and/or decrease response times.

Additives (e.g. $H_2SO_4$) can tune hydrophilic materials to exhibit increased sensitivity to specific gases (e.g. $H_2SO_4$ for ammonia, NaOH for $CO_2$) and increased overall selectivity.

Hydrophilic materials can be manufactured or produced on a common substrate, such as PET. For example, CMC can be dissolved in water, drop cast it on any substrate and then allowed to dry to create the strip of hydrophilic material on the substrate.

Long term stability of electrical measurements of hydrophilic materials can be advantageously increased by using electrochemical impedance spectroscopy. This technology can be used to measure impedance and capacitance change over a wide frequency range when hydrophilic materials are exposed to increasing humidity.

At high humidity (100% relative humidity) electrical measurement stability, reproducibility and response time can be advantageously improved by probing the hydrophilic material at 2 kHz frequency. This benefit occurs because the effects of chemical and physical reactions on the electrodes and inside the hydrophilic sensing material and on the interfaces (e.g. capacitive double-layers) are reduced.

In accordance with another aspect of the invention, there is provided a perishable goods monitoring system for monitoring the freshness and/or condition of a perishable product encapsulated within a package, the system comprising a sensor device, a wireless communication (e.g. RFID or BLE) reader device (e.g. smartphone) and a processing module, said sensor device comprising a fibrous hydrophilic material based electrical sensor and a wireless communication tag chip coupled thereto and being configured to be incorporated in or on a said package, said reader device being configured for wireless communication with said tag by means of wireless communication technology when said reader device is within a predetermined distance of said tag, and said processing module being configured to receive sensor data from said sensor, via said reader device, correlate said sensor data against a stored calibration data set associated with said perishable product and determine thereby data representative of freshness and/or condition of said perishable product.

The sensor device may, beneficially, comprise a sensor device substantially as described above.

Optionally, said fibrous hydrophilic material comprises paper or fabric.

The data representative of freshness and/or condition of said perishable product may comprise or include a predicted use-by date indicative of the last day on which the perishable product is predicted to be fit for consumption. Alternatively, or in addition, the data representative of freshness of said perishable product may comprise an indication as to whether or not the perishable product is currently fit for consumption.

The sensor device is preferably configured to determine a level of at least one water-soluble gas in its vicinity. The water-soluble gas may, for example, comprise ammonia, trimethylamine or carbon dioxide.

The reader device may, optionally, be configured to receive, from said tag, data representative of a level of said water-soluble gas within said package and transmit said data, together with data representative of at least time, in substantially real-time, to said processing module.

The processing module may, optionally, be configured to predict label data (e.g. a use-by date) of said perishable product, based on said sensor data, using a machine learning algorithm.

In accordance with another aspect of the invention, there is provided a perishable goods monitoring system for monitoring the freshness or condition of a perishable product encapsulated within a package, the system comprising a sensor device, a wireless communication reader device and a processing module, said sensor device comprising a fibrous hydrophilic material based electrical sensor and a wireless communication tag chip coupled thereto and being configured to be incorporated in or on a said package, said wireless communication reader device being configured for wireless communication with said wireless communication tag by means of wireless communication technology when said reader device is within a predetermined distance of said tag, and said processing module being configured to receive sensor data from said sensor, via said reader device, correlate said sensor data against a stored calibration data set associated with said perishable product and determine thereby data representative of freshness of said perishable product.

Preferably, said sensor device comprises a substrate incorporating a sensor interface including an ADC, the sensor interface being electrically coupled to a set of electrodes, the sensor device further comprising a strip of fibrous hydrophilic material coupled, on a surface thereof, to a set of electrodes.

Preferably, the substrate incorporates an antenna coupled to the wireless communication tag.

Preferably, said strip of fibrous hydrophilic material comprises cellulose paper, fabric, cotton or fibre glass.

Preferably, said strip of fibrous hydrophilic material is covered or coated with, or has adhered thereto, a thin film or foil of hydrophobic, gas permeable material such as PTFE.

Preferably, said hydrophilic material includes an additive, such as carboxymethyl cellulose, operable to affect its response to humidity.

Preferably, said hydrophilic material includes an additive operable to increase its sensitivity to a specified gas.

Preferably, said additive comprises $H_2SO_4$ operable to increase the sensitivity of the hydrophilic material to ammonia, and/or NaOH operable to increase the sensitivity of the hydrophilic material to $CO_2$.

Preferably, said data representative of freshness or condition of said perishable product comprises or includes a predicted use-by date indicative of the last day on which the perishable product is predicted to be fit for consumption.

Preferably, said data representative of freshness or condition of said perishable product comprises an indication as to whether or not the perishable product is currently fit for consumption.

Preferably, said sensor device is configured to determine a level of at least one water-soluble gas in its vicinity.

Preferably, said water-soluble gas is ammonia.

Preferably, said sensor device is configured to determine a level of at least one water soluble gas in its vicinity by identifying changes in impedance and/or capacitance of the hydrophilic material using, for example, impedance and/or capacitance spectroscopy.

Preferably, said reader device is configured to receive, from said tag, data representative of a level of said water-soluble gas within said package and transmit said data, together with data representative of at least time, in substantially real-time to said processing module.

Preferably, said sensor device is configured to probe said fibrous hydrophilic material at a predetermined frequency, e.g. 2 kHz.

Preferably, said processing module is configured to predict label data of said perishable product, based on said sensor data, using a machine learning algorithm.

In accordance with a further aspect of the invention, there is provided a method of monitoring the freshness and/or condition of a perishable product encapsulated within a package, the system comprising incorporating a sensor device into said package, and providing a wireless communication reader device and processing module, said sensor device comprising a fibrous hydrophilic material based electrical sensor for sensing water soluble gases in its vicinity and an wireless communication tag chip coupled to the sensor, said wireless communication reader device being configured for wireless communication with said tag by means of wireless communication technology when said reader device is within a predetermined distance of said tag, and said processing module being configured to receive sensor data from said sensor, via said reader device, the method further comprising bringing said reader device into close proximity with said sensor device so as to cause said tag chip to obtain sensor data from said sensor device and subsequently transmit freshness or condition data representative of said sensor data to said reader device, and using said processing module to correlate said freshness or condition data against a stored calibration data set associated with said perishable product and determine thereby data representative of freshness or condition of said perishable product.

The sensor device may beneficially comprise a sensor device substantially as described above.

In accordance with a further aspect of the invention, there is provided a method of monitoring the freshness or condition of a perishable product encapsulated within a package, the system comprising incorporating a sensor device into said package, and providing a wireless communication reader device and processing module, said sensor device comprising a paper-based electrical sensor for sensing water soluble gases in its vicinity and a wireless communication tag chip coupled to the sensor, said reader device being configured for wireless communication with said tag by means of a wireless communication technology when said reader device is within a predetermined distance of said tag, and said processing module being configured to receive sensor data from said sensor, via said reader device, the method further comprising bringing said reader device into close proximity with said sensor device so as to cause said tag chip to obtain sensor data from said sensor device and subsequently transmit freshness or condition data representative of said sensor data to said reader device, and using said processing module to correlate said freshness or condition data against a stored calibration data set associated with said perishable product and determine thereby data representative of freshness or condition of said perishable product.

Optionally, said sensor device comprises a substrate incorporating a sensor interface including an ADC, the sensor interface being electrically coupled to a set of electrodes, the sensor device further comprising a strip of fibrous hydrophilic material coupled, on a surface thereof, to a set of electrodes, and optionally wherein the substrate incorporates an antenna coupled to the wireless communication tag.

In accordance with yet another aspect of the invention, there is provided a sensor device for sensing water-soluble gases in a perishable goods monitoring system, the sensor device comprising a substrate incorporating a sensor interface including an ADC, the sensor interface being electrically coupled to a set of electrodes, the sensor device further comprising a strip of fibrous hydrophilic material coupled, on a surface thereof, to a set of electrodes, and optionally wherein the substrate incorporates an antenna coupled to a wireless communication tag.

Preferably, said fibrous hydrophilic material comprises cellulose paper cotton, fibre glass or fabric.

The sensor device may be (adapted) for use in a perishable goods monitoring system comprising a wireless communication reader device, wherein the sensor interface may comprise a wireless communication tag and the substrate may incorporate an antenna coupled to the wireless communication tag.

Preferably, said strip of cellulose paper is covered or coated with a thin film or foil of hydrophobic, gas permeable material.

Preferably, said hydrophobic, gas permeable material is PTFE.

Preferably, said strip of cellulose paper has a thin film or foil of hydrophobic, gas permeable material adhered thereto.

Preferably, said thin film or foil is adhered to said cellulose paper by means of a spray mount adhesive.

Preferably, said cellulose paper is adhered, on a surface thereof, to said set of electrodes by means of a spray mount adhesive.

In accordance with yet another aspect of the invention, there is provided a method of fabricating a sensor device for sensing water-soluble gases in its vicinity and configured to be incorporated into a package containing a perishable product, the method comprising providing a substrate (e.g. PCB) incorporating a set of electrodes and a sensor interface including an ADC coupled to said electrodes, and coupling a surface of a strip of fibrous hydrophilic material (e.g. cellulose paper or fabric) to said set of electrodes.

The method optionally comprises coupling a said surface of said fibrous hydrophilic material to said electrodes by means of a spray mount adhesive.

The method beneficially comprises covering or coating said fibrous hydrophilic material, and/or or individual fibres thereof, with a thin layer of hydrophobic, gas-permeable material, such as PTFE. Beneficially, the method may comprise adhering a PTFE foil or film to the surfaces of said fibrous hydrophilic material by means of a spray mount adhesive. The method may further comprise covering or coating a surface of said fibrous hydrophilic material, and/or individual fibres thereof, with a thin layer of an additive, suspension or solution to enhance sensitivity or selectivity of the sensor. For example, suspensions or solutions containing 'capture molecules' like glutaraldehyde, EDC-NHS or additives like sodium peroxide which induce aldehyde groups on cellulose fibres. Spray coating the paper sensors with these molecules can improve selectivity and/or sensitivity to certain gases (for example selectivity to amine containing volatile organic compounds).

Preferably, said fibrous hydrophilic material comprises cellulose paper or fabric.

Preferably, the method further comprises covering or coating a surface of said fibrous hydrophilic material, and/or individual fibres thereof, with a thin layer of an additive, suspension or solution to enhance sensitivity or selectivity of the sensor.

Preferably, said hydrophobic, gas-permeable material comprises PTFE.

Preferably, the method comprises adhering a PTFE film or foil to the surfaces of said cellulose paper by means of a spray mount adhesive.

Each of the aspects above may comprise any one or more features mentioned in respect of the other aspects above.

The invention extends to methods and/or apparatus substantially as herein described and/or as illustrated in the accompanying drawings.

The invention extends to any novel aspects or features described and/or illustrated herein. In addition, device aspects may be applied to method aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

These and other aspects of the invention will be apparent to a person skilled in the art from the following detailed description.

BRIEF DESCRIPTION OF THE DRAWINGS

Embodiments of the present invention will now be described, by way of examples only, and with reference to the accompanying drawings, in which:

FIG. 1a illustrates graphically the influence of including the additive CMC, in varying quantities, in the fibrous hydrophilic material on stability and response time;

FIG. 2 is a schematic diagram illustrating a PCB forming the basis of a PEGS device for use in the system of FIG. 1;

FIG. 2c illustrates graphically electrical signal stability over time by probing the sensing material at 2 kHz; and FIG. 3 is a machine learning diagram illustrating a function of a processing module in the system of FIG. 1.

DETAILED DESCRIPTION

In the following detailed description, a system and method of monitoring freshness of perishable products will be described, that utilizes a highly sensitive, eco-friendly, near zero-cost, paper-based electrical gas sensor (PEGS) technology for sensing water-soluble gases such as ammonia, trimethylamine, carbon dioxide, etc. at around room temperature or lower (i.e. without requiring heating).

Highly hygroscopic cellulose fibres within paper contain a substantial amount of moisture adsorbed on their surface from the environment. Although cellulose paper looks and feels dry to the touch, it is, in fact, always 'wet', and it is this phenomenon that enables the use of wet chemical methods for the sensing of water-soluble gases, as described in, for example, Güder, F. et al, "Paper-Based Electrical Respiration Sensor", *Chem* 2016, 128(19), 5821-5826 and Alkin, et al, "Paper-Based Printed Impedance Sensors for Water Sorption and Humidity Analysis", Flex. Print. Electron, 2017, 2, 014005, the entire contents of both of which are incorporated herein by reference.

The electrical properties of the thin film of water adsorbed on the cellulose fibres within paper can be probed by measuring the electrical impedance paper using two electrodes printed on the surface of the paper, for example, using conductive carbon ink. When a water-soluble gas is present in the immediate surrounding of the paper, it decrease its impedance, wherein these additional ions come from the dissociation of water-soluble gases in the water layers within the cellulose fibre network. The method and system according to an exemplary embodiment of the present invention applies the above-described PEGS technology to quantitatively monitor the freshness of packaged foods through the sensing of spoilage gases.

Figure 1:
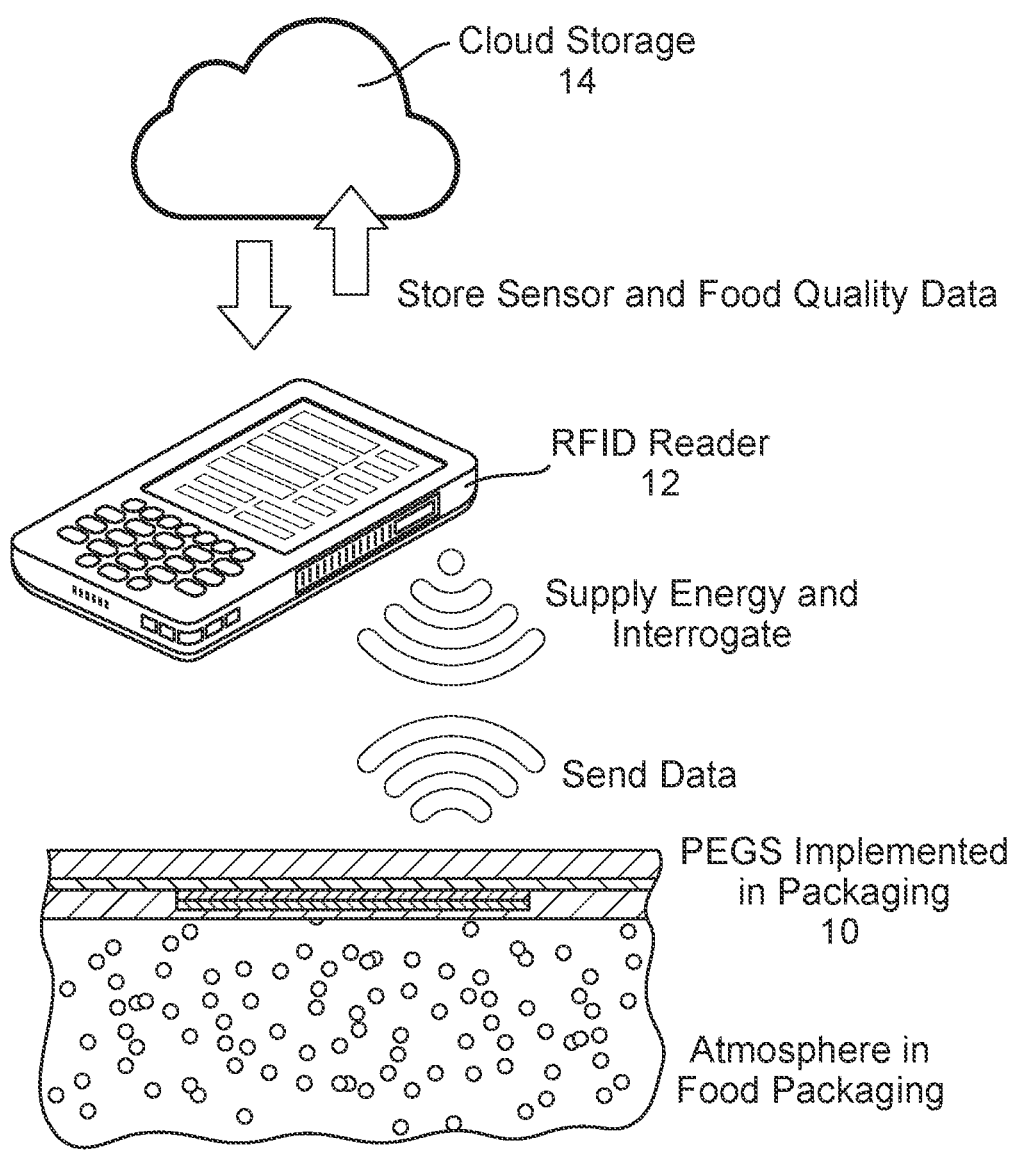
FIG. 1 is a schematic diagram illustrating principal components of a system for monitoring the freshness of a packaged perishable food product.

Referring to FIG. 1 of the drawings, a system according to an exemplary embodiment of the present invention for monitoring and reporting freshness of a packaged perishable food product comprises a PEGS device 10 (including a PEGS) integrated within the package. An RFID (radio frequency identification) reader 12 (either near-field communication (NFC) or far-field RFID (e.g. UHF)) is configured to supply energy (either via the near-field (inductive coupling) or far-field (electromagnetic)) to, and interrogate, the PEGS device 10 when the RFID reader 12 and the PEGS device 10 are sufficiently close together (i.e. <5 cm or so) to allow for wireless data transmission therebetween by means of RFID technology. The RFID reader 12 is configured to transmit freshness data (e.g. sensor data on water-soluble gases) received from the PEGS device 10 to a cloud processing and/or storage facility 14.

As described above, a PEGS simply comprises a strip of cellulose paper which, when in contact with a pair of electrodes, can be probed to provide electrical signals indicative of the presence of certain water-soluble gases in its immediate surroundings. More generally, the sensor may comprise a strip of fibrous hydrophilic material, such as cellulose paper, fabric or fibre glass, which, in contact with a pair of electrodes, can be probed to provide electrical signals indicative of a presence of certain water-soluble gases in its immediate surroundings. In order to effectively integrate the PEGS device into a food package, for example, it is necessary to protect the PEGS, and particularly the cellulose paper, from surrounding moisture, whilst ensuring that water in the form of humidity can still pass through the sensor so that the required water-soluble gases, e.g. ammonia, present in the vicinity of the sensor can still be detected. Advantageously, a hydrophilic material can, for example, be formed on any substrate, such as PET, by dissolving a material such as CMC in water, drop casting it on the substrate and then allowing it to dry. However, other types of hydrophilic material and methods of forming such materials, will be known to a person skilled in the art.

Accordingly, the cellulose paper of the PEGS in the PEGS device 10 is covered with a thin layer of hydrophobic, gas permeable material, such as PTFE. In a preferred exemplary embodiment of the invention, this is achieved by sticking thin PTFE foil onto the cellulose paper using spray mount adhesive or the like. In other embodiments, the individual fibres of the cellulose paper may additionally or alternatively be coated with a thin layer of hydrophobic, gas permeable material.

Additives can be incorporated into the cellulose paper in order to 'tune' the material to exhibit particular responses to humidity and, for example, increase signal stability and decrease response time. One such additive might be carboxymethyl cellulose (CMC), and FIG. 1a illustrates graphically the influence of CMC on stability and response time of cellulose paper. However, other additives may be apparent to a person skilled in the art, depending on the response profile required. Furthermore, additives can also be used to 'tune' the cellulose paper to exhibit increased sensitivity to specific gases. For example $H_2SO_4$ can be used to increase sensitivity to ammonia and NaOH can be used increase sensitivity to $CO_2$, but others may be apparent to a person skilled in the art, depending on the response profile required.

Referring additionally to FIG. 2 of the drawings, the PEGS device 10 comprises a substrate that may, for example, comprise a printed circuit board 16 in the form of a wireless communication (e.g. RIFD) read out board having an antenna 18, a chip in the form of a wireless communication (e.g. RFID) tag 20, and a set of electrodes 22. More generally, the substrate carries the electronics, the electrodes for the sensor, and a chip to support some form of wireless communication technology such as RFID or even Bluetooth Low Energy (BLE), in which case batteries may be used to power the board. The sensor works in high humidity (as compared to other common sensors). It will be appreciated that, in some exemplary embodiments, the sensor material can be the same as the substrate material. In other words, the substrate carrying the electronics and antenna can, for example, be paper-based (e.g. paper-based RFID tag) and the reader, tag and antenna could even be incorporated in the cardboard box (for example) carrying the perishable product—it need not be a separate substrate at all.

Although the PEGS could, for example, be fabricated by printing interdigitated carbon electrodes on cellulose paper and then attaching the complete PEGS to the RFID read out board 16, in this preferred exemplary embodiment of the invention, the electrodes 22 are integrated into the PCB 16 and a piece of PTFE-coated cellulose paper (not shown) is attached to the PCB 16, over and in contact with the electrodes 22, by means of a spray mount adhesive, for example.

The RFID tag 20 includes a built-in sensor interface of a type known to persons skilled in the art. The built-in sensor, which preferably utilizes power received from the RFID reader 12, is configured to connect to the PEGS, and includes an analog-to-digital converter (ADC) which acquires and formats the PEGS's voltage response.

The antenna 18 communicates with, and receives power from, the RFID reader 12 (for near-field RFID e.g. an NFC-enabled smartphone), and the RFID tag 20 converts that power to a useable voltage to be applied to the electrodes 22 and to receive the analog sensor data. Once digitized, the sensor data can be transmitted, via the antenna 14, back to the RFID reader 12.

Figure 2A:
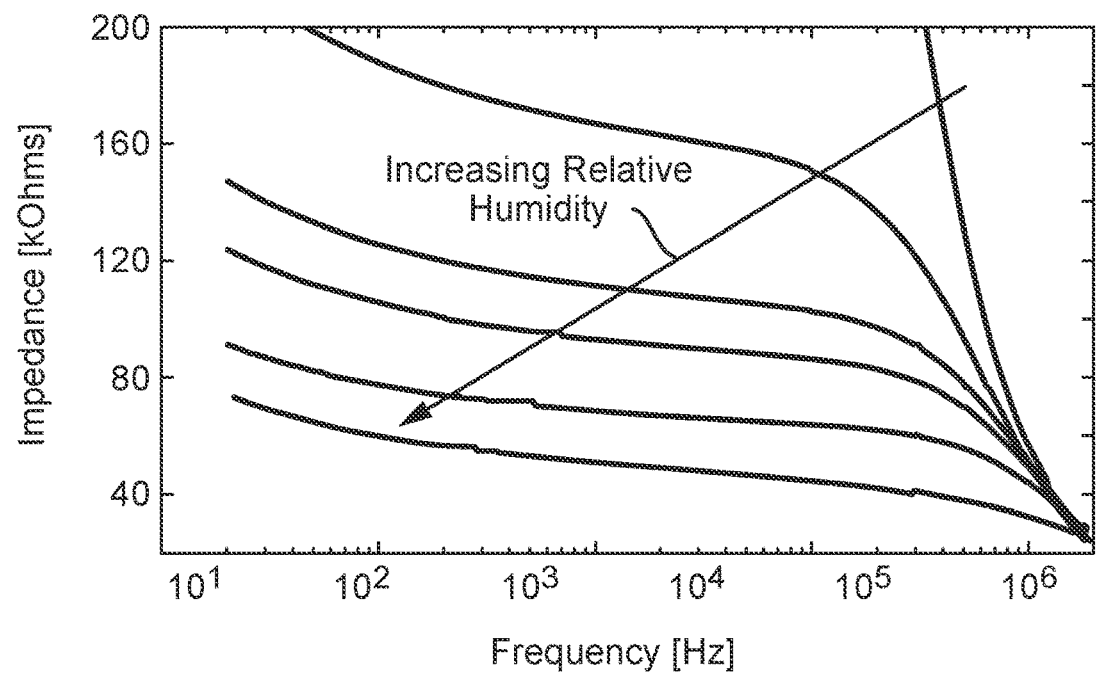
FIG. 2a illustrates graphically an impedance spectroscopy measurement result with increasing relative humidity.
Figure 2B:
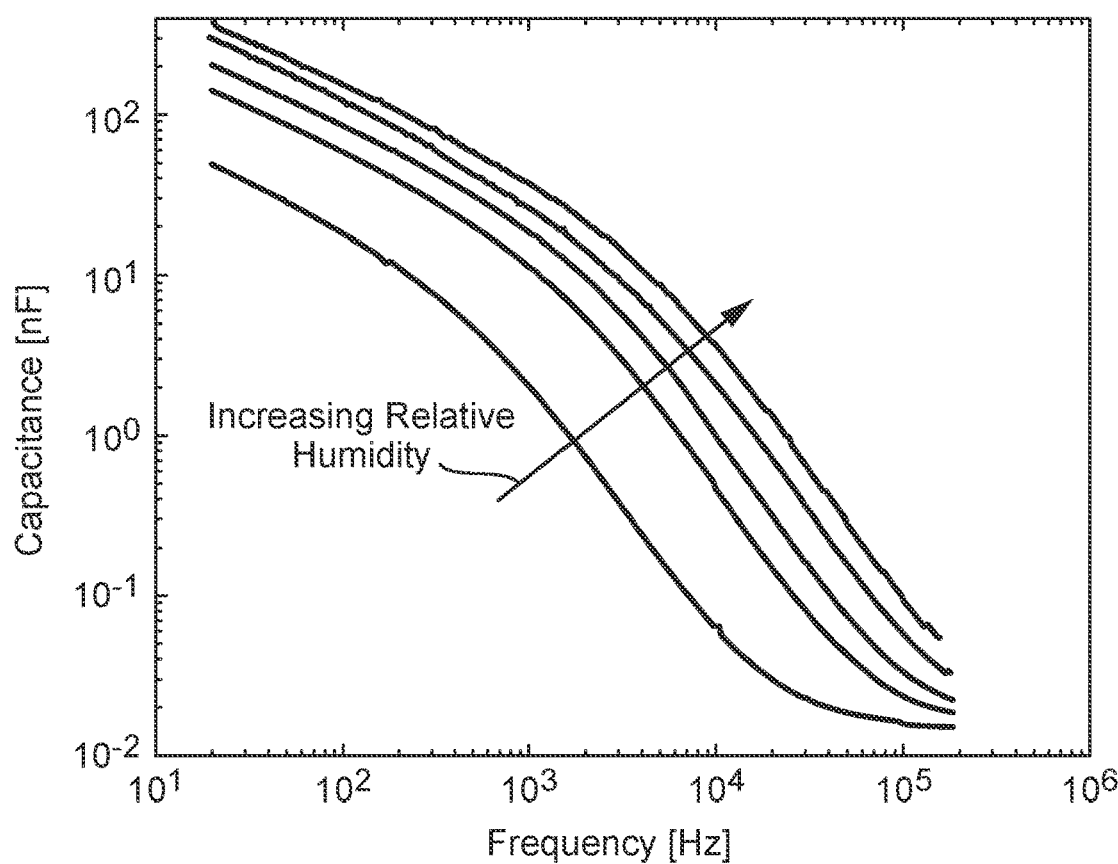
FIG. 2b illustrates graphically a capacitance spectroscopy measurement result with increasing relative humidity.

The PEGS device 10, in use, acts to measure the impedance of the paper in the PEGS between the electrodes 22 to determine the admittance of the PEGS when exposed to water-soluble gases, such as ammonia, wherein the change in admittance is proportional to the water-soluble gas (e.g. ammonia) concentration. In an exemplary embodiment, the long term stability of electrical measurements of the hydrophilic material can used by using electrochemical impedance spectroscopy, wherein impedance and/or capacitance change can be measured over a wide frequency range when the hydrophilic material is exposed to increasing humidity. FIG. 2a illustrates, graphically, impedance spectroscopy results with increasing relative humidity; and FIG. 2b illustrates, graphically, capacitance spectroscopy measurement results with increasing relative humidity.

Furthermore, at high humidity (~100% humidity), a novel measurement method can be deployed to increase electrical measurement stability, reproducibility and response time by probing the hydrophilic material at a predetermined frequency (e.g. 2 kHz), as illustrated in FIG. 2c of the drawings. This advantageous effect occurs because the effects of chemical and physical reactions on the electrodes and inside the hydrophilic sensing material and on the interfaces (e.g. capacitive double-layers) are reduced.

Thus, using a smart packaging system of the present invention, the PEGS device 10 can be used, in conjunction with the RFID reader 12, to non-destructively monitor spoilage of a packaged food product according to the concentration of a food spoilage gas in the vicinity of the PEGS.

Purely by way of example, in the following description, there is described how a system of the present invention can be used to monitor the decomposition or spoilage of fresh meats. However, it will be appreciated that the system could be readily adapted to monitor freshness of various other types of packaged perishable products, which may produce various different water-soluble gases as they spoil/decay, and the present invention is not necessarily intended to be limited in this regard.

Relatively large amounts of TVB-N (total-volatile-basic-nitrogen) are produced when meat products decay. Therefore, TVB-N sensing, using a PEGS device 10 of a system according to an exemplary embodiment of the invention, may be used as an index to assess the quality of meat products, including fish. It should be noted that such an index may be used to monitor the freshness of a meat product, not just whether or not it is still edible.

The main components of TVB-N are $NH_3$ (ammonia) and the related TMA (trimethylamine) and DMA (dimethylamine). In contact with water, all three gases behave similarly: first they partly dissolve in water, according to Henry's law, then dissociate into ions and change the ionic strength of the solution. By measuring the ionic strength of the solution, using a PEGS device 10 according to an exemplary embodiment of the present invention, it is possible to determine the level of TVB-N in the region surrounding the PEGS, and thereby to estimate the freshness of the meat.

The PEGS yields an increase in signal over time as the freshness of the packaged product deteriorates. Although ammonia is considered to be a particularly good indicator in this case, other water-soluble gases may be present, for example trimethylamine or carbon dioxide, which may be used as alternative indicators, especially in relation to other types of perishable food products.

Thus, more generally and as described above, the PEGS device 10 can be used to monitor the freshness of packaged food. It may be used in large packages (e.g. when fish is shipped in bulk in cooled Styrofoam boxes) or in small packages (e.g. point-of-sale fish/meat packaging). The RFID reader 12, e.g. an NFC-enabled smartphone, supplies energy to the RFID tag 20, which is powered for as long as the RFID reader 12 is within a certain range of the PEGS device 10 (e.g. <~5 cm). During this (relatively) short time, the RFID tag 20 uses the PEGS to detect spoilage gases and reports the values back to the RFID reader 12. The RFID reader software may add time and location (and possibly other relevant) data to the data set and transmits it to the cloud server 14.

The RFID tag 20 may store data associated with a particular food product and supplied by the RFID reader 12 when the tag 20 is read for the first time. For example, for a large consignment of fish, this data may include, for example, date of catch, species, location, company and distributor.

All data received, in substantially real-time, at the cloud server 14 may be correlated against known spoilage data for an associated food product, which may be obtained, for example, from the traditional microbial testing currently used to determine use-by dates. As such, based on data received at any time, and correlated against known spoilage data, the cloud processing module is configured to determine a degree of 'freshness', at any time, of the food product. Data representative of that 'freshness' is returned to the RFID reader 12 for display to the user. For example, such data may indicate a predicted use-by date, or it may indicate that the food product has spoiled to a degree that it can no longer be eaten. However, and depending on the source data collected, this data could represent other factors or characteristics associated with the 'freshness' of the product, and the present invention is not necessarily intended to be limited in this regard.

It is envisaged that the cloud processing module could be configured to monitor, in substantially real-time, the freshness or 'condition' of a perishable product and predict future sensor values using a machine learning algorithm on current sensor values, as illustrated schematically in FIG. 3 of the drawings, which shows how measurements from the point-of-use sensor, combined with training data, can be used to: predict difficult-to-measure parameters (e.g. shelf-life, premature opening of the package, leaking package, faulty product etc.) at the point-of-use, using regressors; and predict parameters into the future (e.g. use-by dates), using recurrent neural networks. Available data (e.g. sensor value, time, location, temperature, humidity, producer, species, supply chain details, etc.) can be used to label data and predict the use-by date of the food product. The more data that is collected, the better the model becomes, as each new data point improves the predictions. The collected data sets could also be used to predict/analyse label data to determine if, for example, a food product is incorrectly labelled or erroneously described. The machine learning algorithm, in an exemplary embodiment, is used to predict shelf-life (=> use-by date), by training with microbial/lab measurements. The machine learning algorithm may also be used to predict any other label data e.g. species (for product identification/ fraud prevention), and can also flag any unusual events e.g. low fridge temperature (so consumers/retailers know if their fridges are deficient), or package opening (e.g. leakages or tampering).

Thus, the cloud processing module could be configured to detect, in substantially real-time, from the received data sets, abrupt or abnormal ('unexpected') changes in the gas composition within a package or storage/transport container. This could occur, for example, if modified atmosphere packaging (MAP) is leaking, a package has been opened or otherwise tampered with, a package contains a slightly different product to all similar packages (e.g. a mix of cheaper fish/meat), or the cold chain (during transport/ delivery) was broken or otherwise compromised at some point.

It will be apparent to a person skilled in the art, from the foregoing description, that modifications and variations can be made to the described embodiments without departing from the scope of the invention as defined by the appended claims.

The invention claimed is:

1. A perishable goods monitoring system for monitoring the freshness or condition of a perishable product encapsulated within a package, the system comprising a sensor device, a wireless communication reader device and a processing module;
    said sensor device being configured to be incorporated in or on a said package and comprising:
        a hydrophilic material based electrical sensor;
            wherein said hydrophilic material is provided on a common substrate;
            wherein said hydrophilic material is covered with, or has adhered thereto, a thin film or foil of a gas permeable hydrophobic material;
            wherein said hydrophilic material includes one or more hydrophilic additives; and
        a wireless communication tag chip coupled to the hydrophilic material based electrical sensor;
    said wireless communication reader device being configured for wireless communication with said wireless communication tag chip by means of wireless communication technology when said wireless communication reader device is within a predetermined distance of said wireless communication tag chip; and
    said processing module being configured to receive sensor data from said sensor device, via said wireless communication reader device, correlate said sensor data against a stored calibration data set associated with said perishable product and determine thereby data representative of freshness of said perishable product.

2. The perishable goods monitoring system according to claim 1, wherein said sensor device comprises a sensor interface including an ADC, the sensor interface being electrically coupled to the hydrophilic material based electrical sensor.

3. The perishable goods monitoring system according to claim 2, wherein the sensor device comprises an antenna coupled to the wireless communication tag chip.

4. The perishable goods monitoring system according to claim 2, wherein said hydrophilic material includes a cellulose derivative or carboxymethyl cellulose as hydrophilic additive.

5. The perishable goods monitoring system according to claim 2, wherein said hydrophilic material includes further additive operable to increase its sensitivity to a specified gas, wherein said additive comprises $H_2SO_4$ operable to increase the sensitivity of the hydrophilic material to ammonia, and/or NaOH operable to increase the sensitivity of the hydrophilic material to $CO_2$.

6. The perishable goods monitoring system according to claim 1, wherein said data representative of freshness or condition of said perishable product comprises or includes a predicted use-by date indicative of the last day on which the perishable product is predicted to be fit for consumption and/or an indication as to whether or not the perishable product is currently fit for consumption.

7. The perishable goods monitoring system according to claim 1, wherein said sensor device is configured to determine a level of at least one water-soluble gas in its vicinity.

8. The perishable goods monitoring system according to claim 1, wherein said sensor device is configured to determine a level of at least one water-soluble gas in its vicinity by identifying changes in impedance and/or capacitance of the hydrophilic material.

9. The perishable goods monitoring system according to claim 1, wherein said wireless communication reader device is configured to receive, from said wireless communication tag chip, data representative of a level of said water-soluble gas within said package and transmit said data, together with data representative of at least time, in substantially real-time to said processing module.

10. The perishable goods monitoring system according to claim 1, wherein said sensor device is configured to probe said hydrophilic material at a predetermined frequency.

11. The perishable goods monitoring system according to claim 1, wherein said processing module is configured to predict label data of said perishable product, based on said sensor data, using a machine learning algorithm.

12. The perishable goods monitoring system according to claim 1, wherein said sensor device is configured to determine a level of at least one water-soluble gas in its vicinity by identifying changes in impedance and/or capacitance of the hydrophilic material using impedance and/or capacitance spectroscopy.

13. The perishable goods monitoring system according to claim 1, wherein said sensor device is configured to probe said hydrophilic material at a predetermined frequency of 2 kHz.

14. The perishable goods monitoring system according to claim 1, wherein said hydrophilic material is provided on a common substrate of PET.

15. A method of monitoring the freshness or condition of a perishable product encapsulated within a package, the method comprising:
    incorporating a sensor device into said package, and
    providing a wireless communication reader device and processing module, said sensor device comprising:
        a hydrophilic material based electrical sensor for sensing water soluble gases in its vicinity;
            wherein said hydrophilic material is provided on a common substrate;

wherein said hydrophilic material is covered with, or has adhered thereto, a thin film or foil of a gas permeable hydrophobic material;

wherein said hydrophilic material includes one or more hydrophilic additives; and a wireless communication tag chip coupled to the sensor, said wireless communication reader device being configured for wireless communication with said wireless communication tag chip by means of a wireless communication technology when said wireless communication reader device is within a predetermined distance of said wireless communication tag chip, and said processing module being configured to receive sensor data from said sensor, via said wireless communication reader device;

the method further comprising:

bringing said wireless communication reader device into close proximity with said sensor device so as to cause said wireless communication tag chip to obtain sensor data from said sensor device and subsequently transmit said sensor data to said wireless communication reader device, and receiving said sensor data with said processing module and correlating said received sensor data against a stored calibration data set associated with said perishable product and determining thereby data representative of freshness or condition of said perishable product.

16. A method of fabricating a sensor device for sensing water-soluble gases in its vicinity and configured to be incorporated into a package containing a perishable product, the method comprising providing a substrate incorporating a set of electrodes and a sensor interface including an ADC coupled to said electrodes, and coupling a hydrophilic material to said set of electrodes;

wherein said hydrophilic material is provided on a common substrate;

wherein said hydrophilic material is covered with, or has adhered thereto, a thin film or foil of a gas permeable hydrophobic material;

wherein said hydrophilic material includes one or more hydrophilic additives.

17. The method according to claim 16, wherein said hydrophilic material includes a cellulose derivative or carboxymethyl cellulose as hydrophilic additive.

18. The method according to claim 16, wherein said hydrophilic material comprises $H_2SO_4$ and/or NaOH as further additives.

19. The method according to claim 17, wherein the gas permeable hydrophobic material is PTFE.

20. A sensor device for sensing water-soluble gases in a perishable goods monitoring system, the sensor device comprising a hydrophilic material coupled to a set of electrodes;

wherein said hydrophilic material is provided on a common substrate;

wherein said hydrophilic material is covered with, or has adhered thereto, a thin film or foil of a gas permeable hydrophobic material; and wherein said hydrophilic material includes one or more hydrophilic additives.

* * * * *